United States Patent [19]

Taylor et al.

[11] Patent Number: 5,073,541

[45] Date of Patent: Dec. 17, 1991

[54] TREATMENT OF SMALL CELL LUNG CANCER WITH SOMATOSTATIN ANALOGS

[75] Inventors: John E. Taylor, Upton; Arthur E. Bogden, Hopedale; Jacques-Pierre Moreau, Upton, all of Mass.; David H. Coy, New Orleans, La.

[73] Assignees: Administrators of the Tulane Educational Fund, New Orleans, La.; Biomeasure, Inc., Hopkinton, Mass.

[21] Appl. No.: 231,136

[22] Filed: Aug. 11, 1988

Related U.S. Application Data

[63] Continuation-in-part of Ser. No. 121,937, Nov. 18, 1987, abandoned, which is a continuation-in-part of Ser. No. 70,400, Jul. 7, 1987, abandoned, which is a continuation-in-part of Ser. No. 10,349, Feb. 3, 1987, abandoned, which is a continuation-in-part of Ser. No. 875,266, Jun. 17, 1986, abandoned, which is a continuation-in-part of Ser. No. 775,488, Sep. 12, 1985, abandoned.

[51] Int. Cl.$^5$ .................. A61K 37/02; C07K 5/12; C07K 7/26
[52] U.S. Cl. ........................ 514/9; 514/11; 514/14; 514/15; 514/16; 514/17
[58] Field of Search ............... 530/311, 327, 328, 329; 514/14, 15, 16, 17, 9, 11

[56] References Cited

U.S. PATENT DOCUMENTS

| | | | |
|---|---|---|---|
| 4,133,782 | 1/1979 | Vale, Jr. et al. | 530/311 |
| 4,211,693 | 7/1980 | Rivier et al. | 530/311 |
| 4,282,143 | 8/1981 | Sarantakis | 514/15 |
| 4,291,022 | 9/1981 | Sandrin et al. | 514/15 |
| 4,328,135 | 5/1982 | Sarantakis | 525/54.11 |
| 4,395,403 | 7/1983 | Bauer et al. | 514/15 |
| 4,435,385 | 3/1984 | Bauer et al. | 514/15 |
| 4,485,101 | 11/1984 | Cox et al. | 514/15 |
| 4,650,787 | 3/1987 | Schally et al. | 530/311 |
| 4,703,034 | 10/1987 | Friedinger et al. | 530/311 |
| 4,816,438 | 3/1989 | Spiess et al. | 530/311 |
| 4,820,811 | 4/1989 | Teng | 530/311 |

FOREIGN PATENT DOCUMENTS 0203031 11/1986 European Pat. Off.
2095261A 6/1982 United Kingdom.
WO8601516 3/1986 World Int. Prop. O.

OTHER PUBLICATIONS

Verber, "A Super Active Cyclic Hexapeptide Analog of Somatostatin," Life Sciences, 34: 1371-1378 (1984).
Cai, "Synthesis and Evaluation of Activities of Octapeptide Analogs of Somatostatin," Nature, 292: 55-58 (1981).
Lamberts et al., "Potential Role of Somatostatin Analogues in the Treatment of Cancer," European J. of Clin. Invest., 17: 281-287 (1987).
Setyono-Han et al., "Direct Inhibitory Effects of Somatostatin (Analogues on the Growth of Human Breast Cancer Cells," Cancer Research, 47: 1566-15 (1987).
Moreau et al., "Therapeutic Advances and Perspectives," Life Sciences, 84: 7275-7279 (1987).
Schally et al., "Somatostatin Analogs as Adjuncts to Agonists of Luteinizing Hormone-Releasing Hormone in the Treatment of Experimental Prostate Cancer," Proc. Natl. Acad. Sci., 84: 7275-7279 (1987).
Reubi et al., "Somatostatin Receptors in Human Endocrine Tumors," Cancer Research, 47: 551-558 (1987).
Murphy et al., Chem. Abstracts 104:28911x (1986).
Torres-Alman (Abstract) Chem. Abstracts 102:160733 (1985).
CA Vuk-Pavlovic et al. 97:85726s, vol. 97 1982.
CA Pless et al., 106:770h, vol. 106, 1987.

*Primary Examiner*—Lester L. Lee
*Attorney, Agent, or Firm*—Fish & Richardson

[57] ABSTRACT

A method of treating a mammal suffering from cancer by administering to the mammal somatostatin or an analog thereof, the analog being a hexapeptide analog or higher, in a dosage of at least 25 µg/kg/day.

12 Claims, 4 Drawing Sheets

TREATMENT OF SMALL CELL LUNG CANCER WITH SOMATOSTATIN ANALOGS

This invention was made in the course of work under a grant or award from the U.S. government; therefore, the U.S. government has rights in the invention.

This application is a continuation in part of Taylor et al. U.S. Ser. No. 121,937, filed Nov. 18, 1987 now abandoned, which is a continuation in part of Coy et al. U.S. Ser. No. 070,400, now abandoned, filed July 7, 1987, which is a continuation in part of Coy et al. U.S. Ser. No. 010,349, filed Feb. 3, 1987 and now abandoned, which is a continuation in part of Coy et al. U.S. Ser. No. 875,266, filed June 17, 1986, and now abandoned which is a continuation in part of Coy et al. U.S. Ser. No. 775,488, filed Sept. 12, 1985 and now abandoned.

BACKGROUND OF THE INVENTION

This invention relates to therapeutic peptides.

Somatostatin is a naturally occurring tetradecapeptide having the following amino acid sequence:

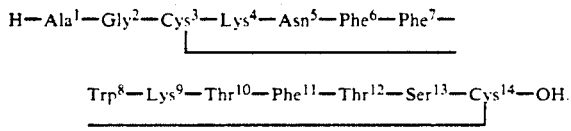

A number of somatostatin analogs exhibiting GH-release-inhibiting activity have been described in the literature, including analogs containing fewer than the naturally occurring fourteen amino acids. For example, Coy et al. U.S. Pat. No. 4,485,101, hereby incorporated by reference, describes dodecapeptides having an N-terminal acetyl group, a C-terminal $NH_2$, D-Trp at position 6, and p-Cl-Phe at position 4. (Herein, when no designation of configuration is given, the L-isomer is intended.)

SUMMARY OF THE INVENTION

In general, the invention features a method of treating a mammal (e.g., a human) suffering from cancer by administering to the mammal somatostatin or an analog thereof containing six or more amino acids, in a dosage of at least 25 μg/kg/day.

Preferably the cancer is characterized by the presence of a solid tumor. If slow growing (less than 0.25 mm/day increase), dosage can be less than 250 μg/kg/day. If the tumor is fast growing, the somatostatin or analog thereof is preferably administered in a dosage of at least 250 μg/kg/day, more preferably at least 500 μg/kg/day.

In another aspect, the invention features a method of treating a mammal (e.g., a human) suffering from cancer characterized by the presence of a solid tumor, by administering to the mammal an effective amount (preferably at least 25 μg/kg/day, and more preferably at least 250 μg/kg/day, even more preferably 500 μg/kg/day) of somatostatin or an analog thereof containing six or more amino acids, administration being carried out at the site of the tumor.

In preferred embodiments of both aspects of the invention, administration is continuous, carried out using pump means or sustained release means. Preferably, in both methods, the somatostatin analog has a four or greater amino acid sequence having at least 20% homology with the core region of somatostatin. (The core region is made up of the amino acids at positions 4, 5, 6, 7, 8, 9, and 10.) More preferably, the somatostatin analog has a six or seven amino acid sequence having at least 20%, even more preferably at least 50%, homology with the core region of somatostatin. Preferably, the somatostatin analog has D-Trp at position 8.

One class of somatostatin analogs which are suitable in the cancer therapy method of the invention are octapeptides of the formula:

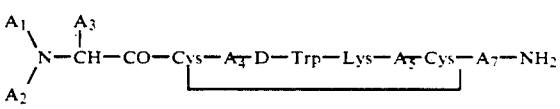

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2-A_6$ (where $A_6$ is pentafluorophenyl, naphthyl, pyridyl, phenyl, or o-, m-, or, more preferably, p-substituted phenyl, where the substituent is a halogen, $NH_2$, $NO_2$, OH, or $C_{1-3}$ alkyl); $A_4$ is o-, m-, or, more preferably, p-substituted X-Phe (where X is a halogen, H, $NH_2$, $NO_2$, OH, or $C_{1-3}$ alkyl), pentafluoro-Phe, or β-Nal; $A_5$ is Thr, Ser, Phe, Val, α-aminobutyric acid, or Ile, provided that when $A_3$ is phenyl, $A_1$ is H, and $A_2$ is H, $A_5$ cannot be Val; and $A_7$ is Thr, Trp, or β-Nal; or a pharmaceutically acceptable salt thereof.

In the formula given above, the configuration of the molecule at the carbon atom to which $A_3$ is bonded is not given, to indicate that the amino acid residue of which $A_3$ is a substituent can have the D- or L- configuration.

Preferred compounds of the above-described formula include

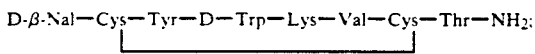

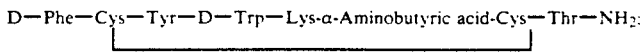

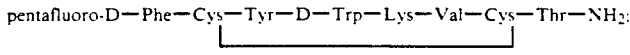

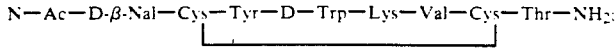

-continued

D-β-Nal—Cys-pentafluoro-Phe—D—Trp—Lys—Val—Cys—Thr—NH₂;

D-β-Nal—Cys—Tyr—D—Trp—Lys—Val—Cys-β-Nal—NH₂;

D—Phe—Cys—Tyr—D—Trp—Lys—Val—Cys-β-Nal—NH₂;

D-β-Nal—Cys—Tyr—D—Trp—Lys-α-aminobutyric acid-Cys—Thr—NH₂;

D-p-Cl—Phe—Cys—Tyr—D—Trp—Lys-α-aminobutyric acid-Cys—Thr—NH₂; and acetyl-D-p-Cl—Phe—Cys—Tyr—D—Trp—Lys-α-aminobutyric acid-Cys—Thr—NH₂.

The compounds which have an aromatic, lipophilic N-terminus have the further advantage of long-lasting in vivo activity.

A therapeutically effective amount of the therapeutic compound and a pharmaceutically acceptable carrier substance, e.g. magnesium carbonate, lactose, or a phospholipid with which the therapeutic compound can form a micelle, together can form a therapeutic composition, e.g. a pill, tablet, capsule, or liquid for oral administration to a patient, a spreadable cream, gel, lotion, or ointment for application to the skin of a patient in need of the compound, a liquid capable of being administered nasally as drops or spray, or a liquid capable of intravenous, parenteral, subcutaneous, or intraperitoneal administration. The most preferred carrier substance is mannitol. The pill, tablet or capsule can be coated with a substance capable of protecting the composition from the gastric acid in the patient's stomach for a period of time sufficient to allow the composition to pass undisintegrated into the patient's small intestine. The therapeutic composition can also be in the form of a biodegradable sustained release formulation for intramuscular administration or, more preferably, administration at the site of a tumor. For maximum efficacy, zero order release is desired. Zero order release can be obtained using an implantable or external pump, e.g., an Infusaid ™ pump (Infusaid Corp., Massachusetts), to administer the therapeutic composition. In addition, the therapeutic composition can be administered in the form of an oil emulsion or dispersion in conjunction with a lipophilic salt such as a pamoic acid.

The method of the invention provides effective cancer therapy, at dosages which can be much higher, e.g., 30 times or greater higher, than the amounts of the compounds which are effective to significantly inhibit release of growth hormone, and yet these high dosages do not cause significant toxic side effects.

Other features and advantages of the invention will be apparent from the following description of the preferred embodiments thereof, and from the claims.

DESCRIPTION OF THE PREFERRED EMBODIMENTS

Drawings

FIGS. 1-4 are graphs illustrating the effect of a somatostatin analog (referred to in the drawings as "BIM23014C") on the growth of tumors.

STRUCTURE

Suitable compounds for cancer treatment are somatostatin or the somatostatin analogs described in the Summary of the Invention, above. Examples are the following analogs, which have been shown to bind to tumor receptors of human small cell lung carcinoma (cell line NCI H69): (binding to such receptors, although possibly related to antitumoral activity, is not necessarily required for such activity.

D-β-Nal—Cys—Tyr—D—Trp—Cys—Val—Cys—Thr—NH₂; D—Phe—Cys—Tyr—D—Trp—Lys—Val—Cys—Nal;

D—Phe—Cys—Phe—D—Trp—Lys—Thr—Cys—Thr—NH₂; and D-p-Cl—Phe—Cys—Tyr—D—Trp—Lys—Val—Cys—Thr—NH₂.

("Nal" refers to naphthylalanine.)

Other suitable somatostatin analogs include the analogs described in Veber et al. (1984) Life Sciences, 34: 1371-1378 e.g., Cyclo Me—Ala Tyr—D—Trp—Lys—Val—Phe Bauer et al., U.S. Pat. No. 4,395,403 e.g., e.g., H—D—Phe—Cys—Phe—D—Trp—Lys—Thr—Cys—Thr—OH Bauer et al., U.S. Pat. No. 4,435,385; Sandrin et al., U.S. Pat. No. 4,291,022; Coy et al., U.S. Pat. No. 4,485,101, described above; and Cai et al. (1986) Proc. Natl. Acad. Sci. U.S.A. 83, 1986-1900

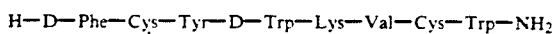

and

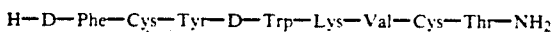

all hereby incorporated by reference.

Synthesis

The synthesis of one octapeptide analog of somatostatin follows. Other analogs can be prepared by making appropriate modifications, within the ability of someone of ordinary skill in this field, of the following synthetic method.

The first step in the preparation of

D-β-naphthyla-

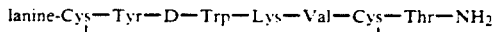

was the preparation of the intermediate tert-butyloxycarbonyl-D-β-naphthylalanine-S-methyl-benzyl-Cys-Tyr-D-Trp-N⁶-benzyloxycarbonyl-Lys-Val-S-methylbenzyl-Cys-O-benzyl-Thr-benzyhydrylaminine resin, as follows.

Benzhydrylamine-polystyrene resin (Vega Biochemicals, Inc.) in the chloride ion form was placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin was stirred with Boc-O-benzyl-threonine and diisopropylcarbodiimide (1.5 mmole each) in methylene chloride for 1 h and the resulting amino acid resin was then cycled through steps (a) to (g) in the above wash program. The following amino acids (1.5 mmole) were then coupled successively by the same procedure:

Boc—S-methylbenzyl-Cys, Boc—Val,
Boc—Nε-benzyloxycarbonyl-lysine, Boc—D—Trp, Boc—Tyr,
Boc—S-methylbenzyl-Cys, Boc—D-β-naphthylalanine.

The resin was washed and dried and then mixed with anisole (4 ml) and anhydrous hydrogen fluoride (36 ml) at 0° C. and stirred for 45 min. (one can also use thioanisole, trifluoroacetic acid, and trifluoromethane sulfonic acid at a ratio of 1:90:9, for 6 h). Excess hydrogen fluoride was evaporated rapidly under a stream of dry nitrogen and free peptide precipitated and washed with ether. The crude peptide was then dissolved in 800 ml of 90% acetic acid to which was added $I_2$ in methanol until a permanent brown color was present. The solution was then stirred for 1 h before removing the solvent in vacuo. The resulting oil was dissolved in a minimum volume of 50% acetic acid and eluted on a column (2.5×100 mm) of Sephadex G-25. Fractions containing a major component by uv absorption and thin layer chromatography were then pooled, evaporated to a small volume, and applied to a column (2.5×50 cm) of Whatman LRP-1 octadecylsilane (15-20 uM).

The column was eluted with a linear gradient of 10-50% acetonitrile in 0.1% trifluoroacetic acid in water. Fractions were examined by thin layer chromatography and analytical high performance liquid chromatography and pooled to give maximum purity and if desired, a different salt prepared, e.g., acetate or phosphate. Repeated lyophilization of the solution from water gave 170 mg of the product as a white, fluffy powder.

The product was found to be homogeneous by Hplc and Tlc. Amino acid analysis of an acid hydrolysate confirmed the composition of the octapeptide.

The octapeptides of the invention having the formulae

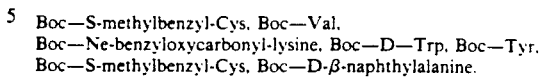

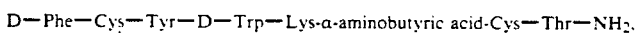

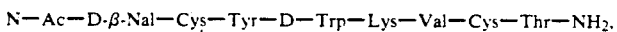

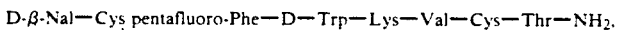

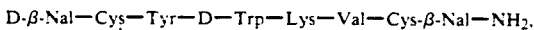

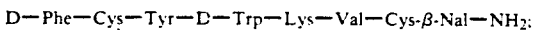

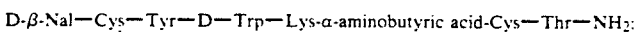

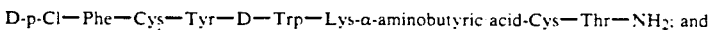

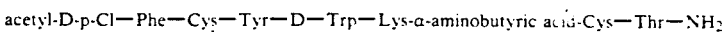

were made according to methods analogous to those described above.

Use

The invention provides effective treatment for cancers, particularly solid tumor carcinomas such as small cell lung carcinoma. Other cancers which can be treated include bone, cartilage, pancreas (endocrine and exocrine), prostate, and breast cancers.

The above-described compounds, and somatostatin and its hexapeptide or higher analogs generally, are useful in the treatment of cancer when administered as described above. The anti-cancer agent is preferably administered directly to the site of the cancerous tumor; indirect, e.g., oral, administration is not as preferred because it requires higher dosages. The agents generally have on the order of a 6 hour lifetime in vivo, and therefore four treatments per day are preferred if non-continuous administration is used, e.g., intravenous injections, as are generally necessary for inaccessible tumors.

The octapeptide somatostatin analog

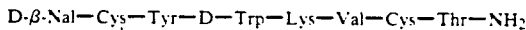

was tested for its ability to inhibit the proliferation of cells of tumors; the results are given in FIGS. 1-4.

Figure 1:
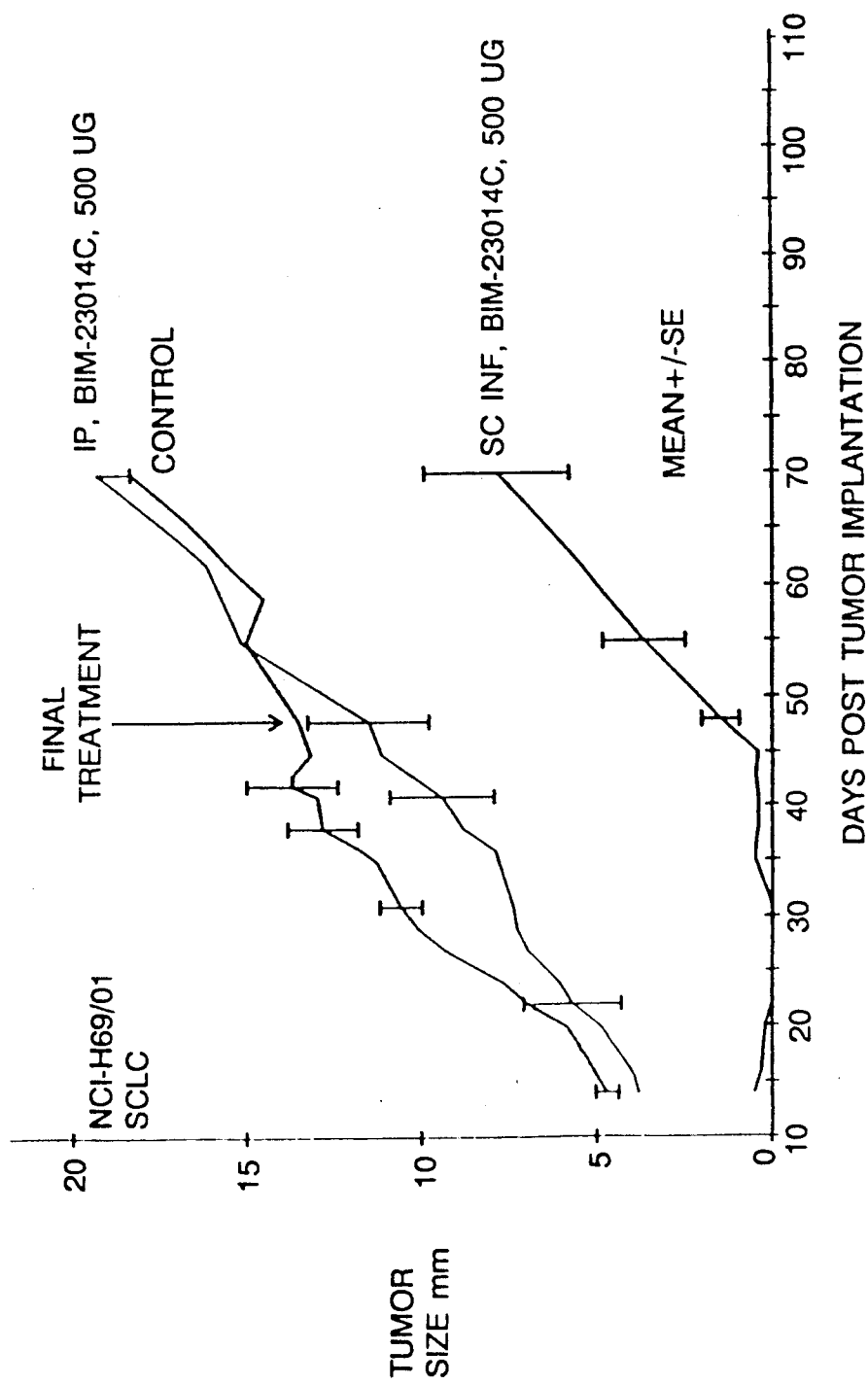
FIGS. 1 and 2 show the effect of the analog on human small cell carcinoma (line NCI-H69), which is a fast growing tumor (0.33 mm/day), implanted in athymic mice. The analog, when administered at the site of the tumor, exhibited a marked effect on the tumor.
Figure 2:
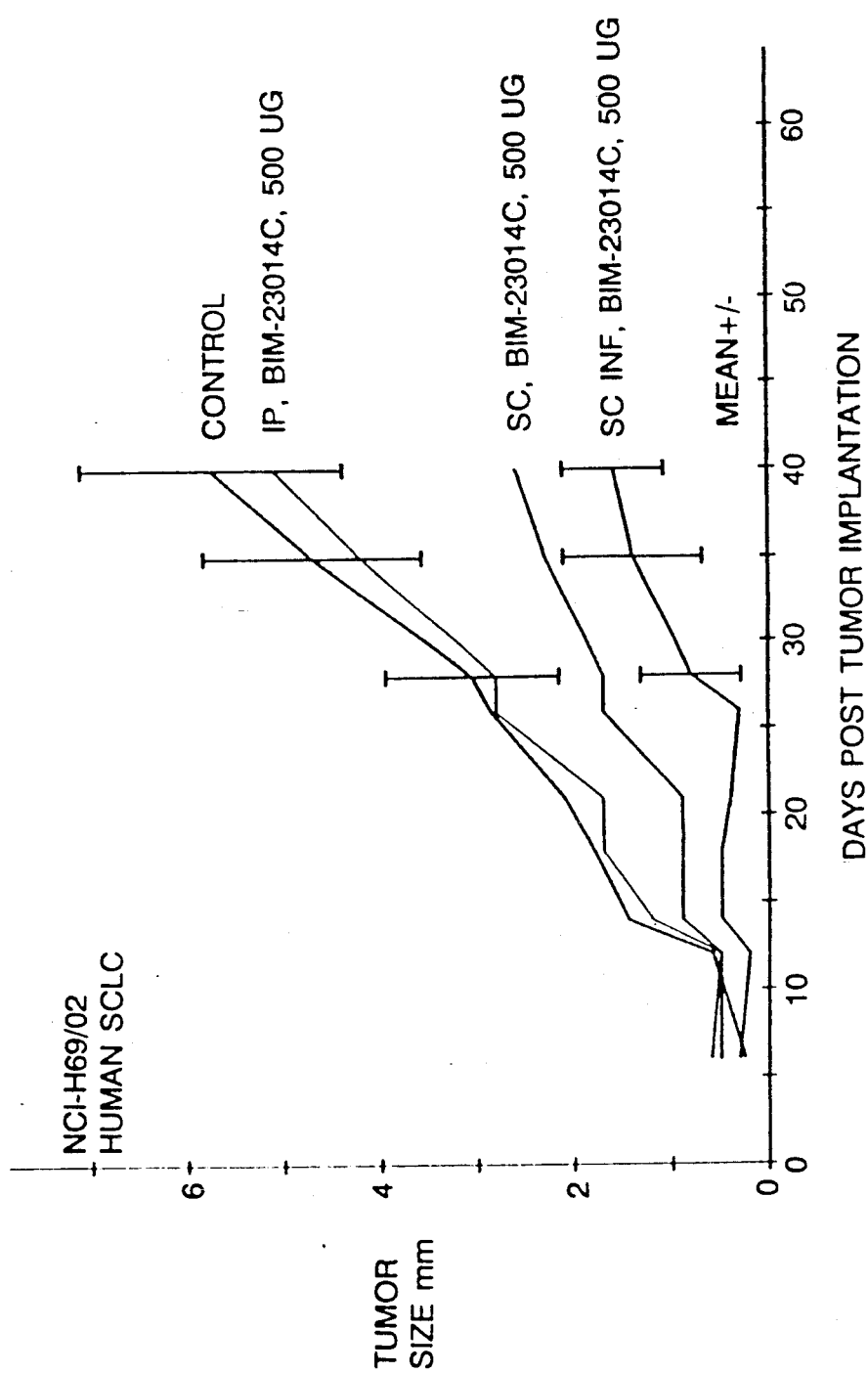
Figure 3:
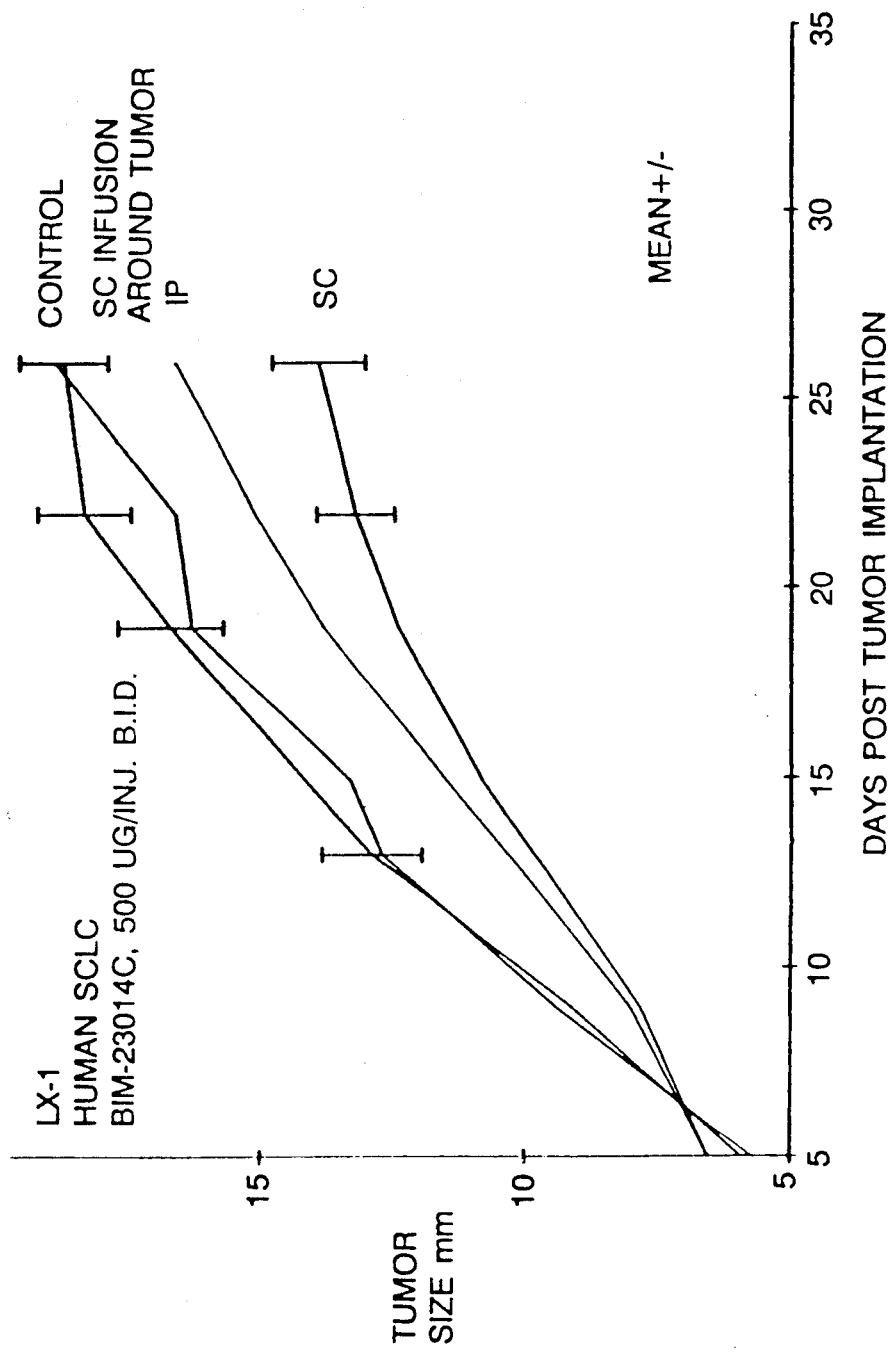
FIG. 3 shows the effect of the same analog on the rapidly growing (0.77 mm/day) cancer human oat cell carcinoma (line LX-1).
Figure 4:
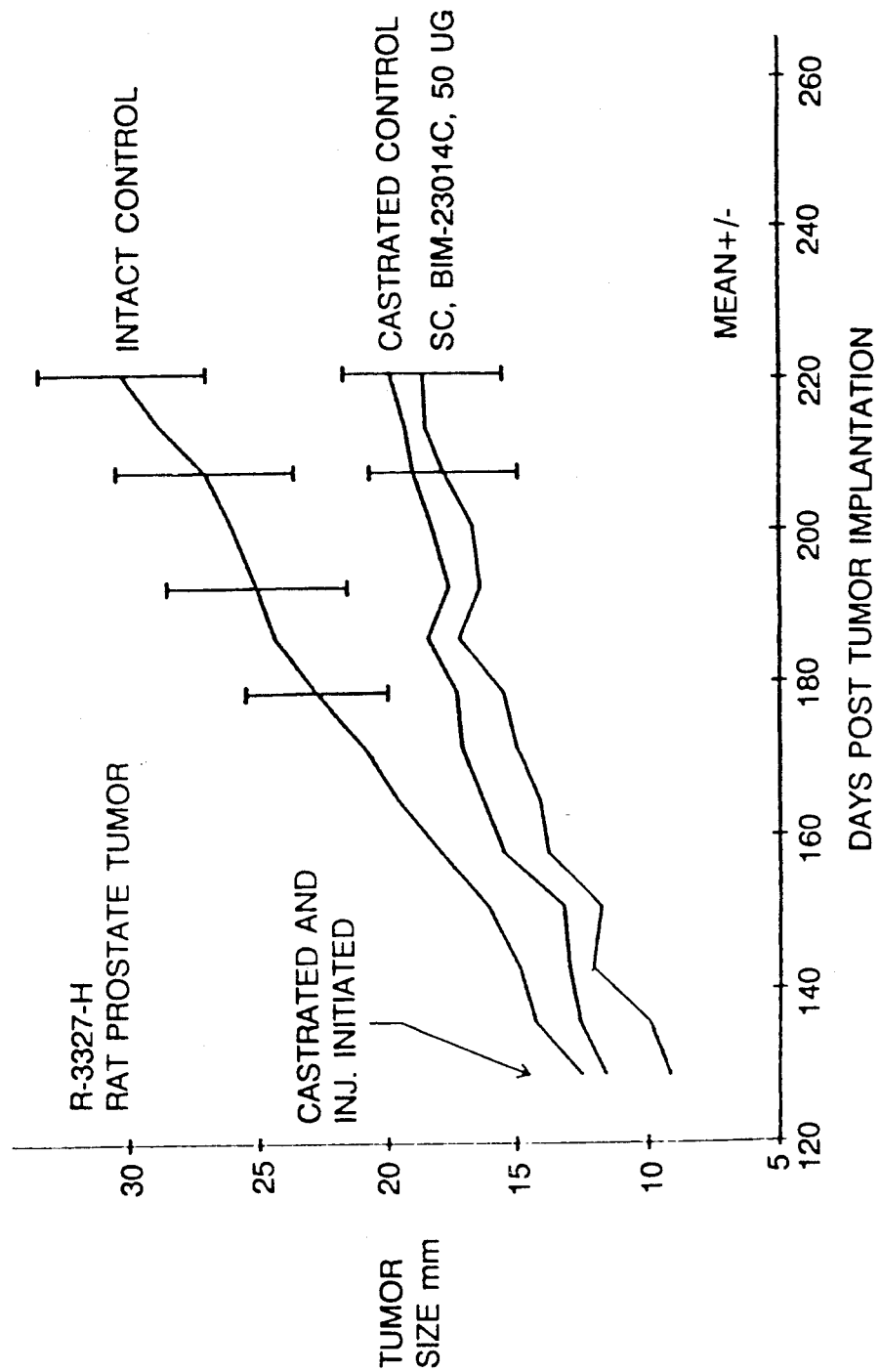
FIG. 4 shows the effect of the same analog on a slow growing (0.19 mm/day) rat prostate tumor.

Other embodiments are within the following claims.

We claim:

1. A method of treating small cell lung cancer in a mammal comprising administering an effective amount of somatostatin analog of the formula:

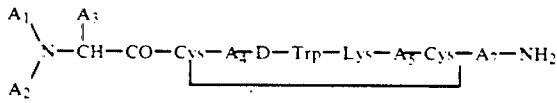

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkynyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2$-$A_6$ (where $A_6$ is pentafluorophenyl, napthyl, pyridyl, phenyl, or o-, m-, or p- substituted phenyl, where the substituent is a halogen, $NH_2$, $NO_2$, $OH$, or $C_{1-3}$ alkyl); $A_4$ is o-, m-, or p-substituted X-Phe (where X is a halogen, H, $NH_2$, $NO_2$, $OH$ or $C_{1-3}$ alkyl), pentafluoro-Phe, or $\beta$-Nal; $A_5$ is Thr, Ser, Phe, Val, α-aminobutyric acid, or Ile, provided that when $A_3$ is phenyl, $A_1$ is H, and $A_2$ is H, $A_5$ cannot be Val; $A_7$ is Thr, Trp, or $\beta$-Nal; and all amino acid residues are linked via an amide bond; or a pharmaceutically acceptable salt thereof.

2. The method of claim 1 wherein said tumor is characterized by the presence of a solid tumor and said administration is carried out continuously using pump means or sustained release means.

3. The method of claim 1 wherein said somatostatin or an analog thereof is

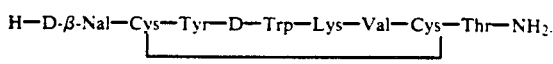

4. The method of claim 3 wherein said tumor is characterized by the presence of a solid tumor and said administration is carried out continuously using pump means or sustained release means.

5. A method of treating small cell lung cancer in a mammal comprising administering an effective amount of somatostatin analog of the formula:

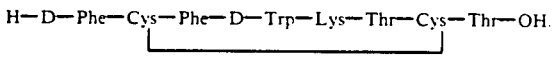

6. The method of claim 5 wherein said tumor is characterized by the presence of a solid tumor and said administration is carried out continuously using pump means or sustained release means.

7. A method of treating small cell lung cancer in a mammal comprising administering an effective amount of somatostatin analog of the formula:

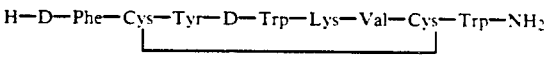

8. The method of claim 7 wherein said tumor is characterized by the presence of a solid tumor and said administration is carried out continuously using pump means or sustained release means.

9. A method of treating small cell lung cancer in a mammal comprising administering an effective amount of somatostatin analog of the formula:

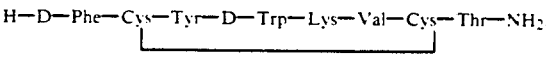

10. The method of claim 9 wherein said tumor is characterized by the presence of a solid tumor and said administration is carried out continuously using pump means or sustained release means.

11. A method of treating small cell lung cancer in a mammal comprising administering an effective amount of somatostatin analog of the formula:

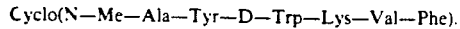

12. The method of claim 11 wherein said tumor is characterized by the presence of a solid tumor and said administration is carried out continuously using pump means or sustained release means.

* * * * *